(12) United States Patent
Borders et al.

(10) Patent No.: US 6,613,889 B2
(45) Date of Patent: Sep. 2, 2003

(54) METHOD FOR PREPARING SALTS OF POLYENE MACROLIDE ESTERS

(75) Inventors: Donald B. Borders, Suffern, NY (US); William V. Curran, Pearl River, NY (US)

(73) Assignee: BioSource Pharm, Inc.

( * ) Notice: Subject to any disclaimer, the term of this patent is extended or adjusted under 35 U.S.C. 154(b) by 0 days.

(21) Appl. No.: 09/935,347

(22) Filed: Aug. 23, 2001

(65) Prior Publication Data

US 2003/0040610 A1 Feb. 27, 2003

(51) Int. Cl.⁷ .................................................. C07H 1/00
(52) U.S. Cl. ....................................... 536/6.5; 536/18.5
(58) Field of Search .................................. 536/6.5, 18.5

(56) References Cited

U.S. PATENT DOCUMENTS 4,041,232 A    8/1977    Sipos et al.
4,308,375 A    12/1981   Tang
5,981,721 A    11/1999   Mohan

*Primary Examiner*—Elli Peselev
(74) *Attorney, Agent, or Firm*—Stanley J. Yavner

(57) ABSTRACT

This method is for preparing salts of amphotericin B methyl ester and other polyene macrolide esters. The steps of the process involve methylation by use of cesium carbonate for converting to methyl ester and significantly reducing side products, which are over methylation products. The free base-Schiff base mixture is converted to amphotericin B methyl ester hydrochloride or some other salt form, by using tetrahydrofuran-water to dissolve the mixture for acid treatment to obtain the salt. The aldehyde liberated during salt formation is removed by centrifuging, as to any precipitated aldehyde, and the aldehyde remaining in solution is removed by eluting the solution through a reverse phase adsorbent to obtain amphotericin B methyl ester hydrochloride as a yellow powder.

7 Claims, No Drawings

METHOD FOR PREPARING SALTS OF POLYENE MACROLIDE ESTERS

FIELD OF THE INVENTION

This invention relates to a method for preparing polyene salts which are water soluble compounds for use as antifungal agents. More particularly, this invention relates to a process for producing high quality antifungal products in a manner that is notable for avoiding reagents that could be very explosive and even highly toxic, and side products, avoiding over acidification, and avoiding removing aldehydes liberated during salt formation by approaches that result in emulsions which are difficult to break.

BACKGROUND OF THE INVENTION

Methods already exist for preparing salts of polyene macrolide antifungal antibiotic esters. The salts of these compounds are highly water soluble and have excellent antifungal activity in vitro and in animals. For instance, U.S. Pat. No. 5,981,721 issued Nov. 9, 1999 to Mohan involved the use of diisopropylethyl amine to accomplish methylation, which results in less than optimal conversion to methyl ester and increases the side products which are over methylation products. Methods previous to Mohan are tedious, easily lead to acid degredation products, and do not apply directly to esters synthesized by methods involving a Schiff base protecting group. An older patent, U.S. Pat. No. 4,041,232, issued Aug. 9, 1977 to Sipos, et al, describes methods of converting the pure free base esters to salts, and relies upon a two-phase reaction (solid-liquid) by adding acid to the insoluble mixture in water. Undesirable side products, caused by over-acidification can result. Also, the two-phase reaction process, in most cases, failed to minimize the over acidification; and the process is slow, when minimizing the over-acidification is attempted.

Still further, the previous methods remove aldehyde liberated during salt formation by solvent extraction, but this approach results in emulsions that are difficult to break.

At pH levels less than 4.0, amphotericin B methyl ester (AME) is very unstable (Bonner, J., et al, Antibiotics, 28, 132, 1975). Another aspect to forming salts from the Schiff bases is the formation of colloids when these components are in contact with water. The colloids complicate the removal of residual aldehydes and generally result in a loss of products by these prior art methods.

Lastly, as to background, Tang U.S. Pat. No. 4,308,375, issued Dec. 29, 1981, relates generally to the same subject matter as the present invention. Nevertheless, Tang who provides a method for purifying water-insoluble polyene antibiotics, accomplishes his process, but without a Schiff base. For getting rid of gram positive and gram negative bacteria, Tang employs an ion exchange column, into which amphotericin B rich methanol is placed for the purification part of the process. The relationship with the present invention is that Tang uses an ion exchange column for purification, but otherwise presents a vastly different method unrelated to the production of a high quality antifungal, which uses tetrahydrofuran to convert a free base-Schiff base mixture to a salt form, in a single phase liquid reaction, or which uses cesium carbonate to produce a free base-Schiff base mixture. In the present invention reverse phase adsorption with an adsorption column is used to remove aldehyde. Therefore, many of the drawbacks mentioned above are likewise applicable to the Tang process.

OBJECTS AND SUMMARY OF THE INVENTION PROCESS

Accordingly, a primary object of the present invention is to provide a method of methylation, which provides better conversion to the methyl ester and significantly reduces the side products which are over methylation products.

A further object of the present invention is to provide a single-phase liquid reaction to convert free base-Schiff base mixture to amphotericin B methyl ester (hereinafter AME) hydrochloride or some other salt form, thereby avoiding conversion to salts by two-phase reactions and the over acidification which results therefrom to form undesirable side products.

A still further object of the present invention is to provide reverse phase adsorption to readily remove aldehyde liberated during salt formation, instead of removing the adlehyde by solvent extraction, which results in emulsions that are difficult to break.

These and other objects of the present invention are provided in a method which features the use of cesium carbonate for converting, by methylation, to methyl ester, with methyl iodide, dimethyl sulfate or other methylating agents. To convert the free base-Schiff base mixture to AME hydrochloride, or some other salt form, the method of the present invention uses tetrahydrofuran (hereinafter THF)—water to dissolve the mixture for the acid treatment to obtain the salt. The THF is then removed by azeotroping, and the resulting water soluble salt of AME in water is recovered by freeze drying. The aldehyde liberated during salt formation is removed by centrifuging, which eliminates any precipitated aldehyde. The significant amount of aldehyde remaining in solution is removed by eluting the solution through the reverse phase adsorbent.

DETAILED DESCRIPTION OF THE INVENTION

Amphotericin B is a polyene macrolide antibiotic useful in a variety of applications, such as the treatment of systemic human fungal diseases and fungal plant infections. Amphotericin B and its methyl ester, AME, have also been shown to have various attributes as an anti-protozoan, with some anti-viral activity.

In order to provide a detailed description of the present invention, in the form of a method for preparing salts of polyene macrolide esters, which utilizes cesium carbonate to reduce the amount of side products, and is more reproducible than methods of the prior art. This invention process, is now described in connection with the preparation of AME. The use of cesium carbonate as a base during the methylation part of the process, with methyl iodide, provides better conversion to the methyl ester and significantly reduces the side products which are over methylation products. Likewise, even before the previously mentioned Mohan patent, which uses diisopropylethyl amine, methylations were done with diazomethane, but this reagent is very explosive and highly toxic. A single phase liquid reation is used to convert the free base-Schiff base mixture to AME hydrochloride or some other salt form. The process used THF to dissolve the mixture for the acid treatment in order to obtain the salt. The THF is removed by azeotroping, and the resulting water soluble salt in water is recovered by freeze drying, thus avoiding the two phase reactions of the prior art, which added acid to the insoluble mixture of free base-Schiff base in water. Thereby, the tendency for over acidification is diminished, and the overall process is simplified.

In order to facilitate removal of the aldehyde protective group of the Schiff base and to form the salt of the liberated free base ester, the Schiff base is stirred in water overnight, centrifuged and the insoluble product dried by lyophilization. HPLC and 300 Mhz NMR indicate that the product contains some p-chlorobenzaldehyde and is usually about a 50/50 mixture of the desired methyl ester and the corresponding Schiff base. The mixture is stirred in ethyl acetate to remove the excess aldehyde. The product is then dissolved in a solvent which is inert to the materials, is miscible with water, and can be removed from an aqueous solution as an azeotrope. Tetrahydrofuran or acetonitrile fulfil these requirements. Solvents such as methanol which do not azeotrope with water can also be used but would require evaporation to dryness in order to remove and this would complicate redissolving. A solution of amphotericin B methyl ester Schiff base/free base in tetrahydrofuran is diluted with water to approximately 75% THF but maintained in solution. To this solution is added dilute hydrochloric acid until the appropriate pH is reached. This causes the hydrolysis of the Schiff base and forms the hydochloride salt of amphotericin B methyl ester. The tetrahydrofuran is then removed as an azeotrope with water to obtain an aqueous solution of the AME.HCl and some insoluble material containing part of the aldehyde. The residual aldehyde in the aqueous solution of the AME.HCl is an impurity which can not be readily removed by filtration, centrifuging, or solvent extraction. To remove the aldehyde, the aqueous solution of AME.HCl is passed over a reverse phase support such as Amberlite® XAD-2 (Amberlite is a registered trademark of Rohm & Haas of Philadelphia, Pa.) pre-washed with methanol and then water. The aldehyde adsorbs to the resin and essentially all the AME.HCl elutes through. The effluent from the resin is freeze-dried to obtain AME.HCl as a yellow powder which is highly soluble in water.

During the process of washing the Schiff base with water, some of the Schiff base and the liberated ester free base are dispersed in the water wash as a colloidal suspension. The aqueous colloid is readily removed from the solid Schiff base and ester free base by centrifuging. To recover product from the colloid, ammonium chloride is dissolved into the suspension at 3% weight/volume and the mixture (pH~5) is allowed to stand at 4 degrees Centigrade for 20 hours. This process converts the colloid material to AME.HCl and precipitates it from the aqueous solution. The precipitated AME.HCl is separated from the solution, dissolved in water, the residual aldehyde is removed with Amberlite® XAD-2 as described above, and the resulting aqueous solution freeze dried to obtain AME.HCl as a yellow powder.

Additionally, relating to, for instance, examples 8, 9 and 12 of the following examples, a process for preparing esters of polyene macrolide is set forth. Firstly, a mixture containing an amphoteric polyene macrolide antifungal selected from the group consisting of amphotericin B, nystatin, pimaricin, amphotericin A, rimocidin, partricin and their derivatives and anhydrous dimethylformamide is allowed to react with an aldehyde followed by the addition of cesium carbonate and methyl iodide, to produce a free base-Schiff base mixture of the methyl ester. The free base/Schiff base mixture of the ester is converted to the relatively pure free base of the ester by methods involving bisulfite or Girards T reagent and dialysis. The free base in a single phase liquid reaction is converted to amphotericin B methyl ester hydrochloride or some other salt form by using tetrahydrofuran and water to dissolve the free base for acid treatment to obtain the salt. The tetrahydrofuran is removed by azeotroping, and the water soluble salt of amphotericin B methyl ester in the water is recovered by freeze drying.

In order to illustrate the improvement enabled by the present invention, a series of laboratory procedures were carried out, beginning with the state-of-the-art method for the methylation of amphotericin B. Such examples of laboratory activity are set forth in the following examples, showing the efficacy of the present invention.

EXAMPLES

1) Improved Method for Methylation of Amphotericin B

Amphotericin B (1.015 g., 1.10 mmols.) and p-chlorobenzaldehyde (0.390 g., 2.77 mmols.) in 10 ml. of anhydrous dimethylformamide (DMF) was stirred at room temperature for 30 min. to affect complete solution. Cesium carbonate (0.356 g., 1.09 mmols,) was added and stirred for about 30 min. followed by the addition of methyl iodide (0.070 ml., 1.14 mmols.). The mixture was stirred at room temperature for 45 min. at which point HPLC indicated 75% conversion to the desired product. An additional 0.35 ml. (0.058 mmols.) of methyl iodide was added and stirred an additional 2.0 hrs. The reaction mixture was poured into 100 ml. of t-butylmethyl ether and filtered. The resulting solid was stirred in 50 ml. of water for 4 hrs. (pH 9.35), centrifuged and washed with two further portions of water by centrifuging (final pH=7). The resulting solid was lyophilized and stirred in 25 ml. of ethyl acetate, filtered and dried to give 0.876 g. of the desired product. H NMR at 400 MHz in DMSO-d6 showed aromatic protons (7.52 PPM, d, 8.5 Hz and 7.83 PPM, d, 8.5 Hz) for the Schiff base and the integration indicated a 50/50 mixture of the Schiff base and AME.$E^{1\%}_{1\ cm}$=1300 at 382 nm.

2) Conversion of Schiff Base/Free Base to AME.HCL

Amphotericin B methyl ester Schiff base/free base, 11.7 g. was dissolved in 250 ml. of tetrahydrofuran:water (200:50) and a solution of 65 ml. of 0.1 N hydrochloric acid was added dropwise with stirring. The tetrahydrofuran was evaporated in-vacuo (40° C.) as an azeotrope and water (250 ml.) was added. The mixture was centrifuged to remove some of the aldehyde and other impurities. The aqueous supernatant was decanted and passed through an Amberlite® XAD-2 column (3×32 cm.). The solution was lyophilized to afford 9.3 g. of the AME.HCL.$E^{1\%}_{1\ cm}$=1472 at 382 nm, FABMS m/z 938 (M+H)$^+$.

3) Recovery of AME.HCl from Colloidal Suspension of Free Base

The water washes from the solid described in example 1 formed a yellow colloid by suspension of some of the solid product. The colloid was very stable and could not be separated by filtration or centrifuging. Ammonium chloride, 25.5 gm, was dissolved in the combined 850 ml washes to give a 3% weight/volume mixture, pH~5.0, which was allowed to stand at 4° C. for 20 hours. This process converted the coloidal material to AME.HCl and at this concentration the ammonium chloride precipitated the product. The resulting AME.HCl was separated by centrifuge, washed with a small amount of 1% aqueous ammonium chloride, blotted to dry, dissolved in water, passed through an Amberlite XAD-2 column to remove residual aldehyde, and freeze-dried to obtain 550 mg of AME.HCl as a yellow powder.

4) Improved Method for Methylation of Nystatin

Nystatin (1.0164 g., 1.098 mmols.) was dissolved in 5 ml. of DMF and treated as described in Example 1 above with cesium carbonate except that two equivalents of methyl iodide were used to afford 0.6215 g. of product, $E^{1\%}_{1\ cm}$=528 at 304 nm in MeOH. 1H NMR (400 MHz DMSO-d6) revealed this to be a 2:1 mixture of the nystatin methyl ester free base and the N-p-chlorobenzilidene derivative.

5) Conversion of Schiff Base/Free Base to Nystatin Methyl Ester Acetate

The product described in Example 4 above was dissolved on 10 ml. of tetrahydrofuran:water (1:1) solution and added 0.023 ml. of acetic acid. The tetrahydrofuran was removed in-vacuo at 35 C and the resulting aqueous solution was passed through an Amberlite® XAD-2 column (1.5×21 cm.) as described in Example 2 and lyophilized to afford nystatin methyl ester acetate, 0.2341 g, $E^{1\%}_{1\ cm}$=441 at 304 nm in MeOH, $C_{48}H_{78}NO_{17}$ FABMS:m/z 940 $(M+H)^+$.

6) Improved Method for Methylation of Pimaricin

Pimaricin (0.955 g., 1.494 mmols.) was dissolved in 5 ml. of DMF and treated as described in Example 4 above with cesium carbonate and two equivalents of methyl iodide to afford 0.5124 g. of product, $E^{1\%}_{1\ cm}$=730 at 303 nm. $^1$H NMR (400 MHz, DMSO-d6) revealed this to be about 2:1 mixture of the pimaricin methyl ester free base and the N-p-chlorobenzilidene derivative.

7) Conversion of Pimaricin Schiff Base/Free Base to Pimaricin Methyl Ester Hydrochloride The product described in Example 6 above was dissolved on 10 ml. of tetrahydrofuran:water (1:1) and a solution of 5 ml. of 0.1 N hydrochloric acid was added dropwise. The tetrahydrofuran was removed in-vacuo at 35° C. and the resulting aqueous solution was passed through an Amberlite® XAD-2 column (1.5×21 cm.) as described in Example 2 and lyophilized to afford pimaricin methyl ester hydrochloride 0.2550 g, having the typical tetraene chromophore, $E^{1\%}_{1\ cm}$=910 at 303 nm in MeOH, $C_{34}H_{49}NO_{13}$ FABMS:m/z 679 $(M+H)^+$.

8) Conversion of Amphotericin B Schiff Base to Free Base

A mixture of the amphotericin B methyl ester and N-p-chlorobenzilidene derivative (2.5 g.) and sodium bisulfite (2.64 g.) was stirred for 2.0 hrs. in 75 ml. of water. The mixture was centrifuged, decanted and washed with two more portions of water by centrifuging. The resulting solid was lyophilized to afford 1.05 g. of the free base ester, $E^{1\%}_{1\ cm}$=1293 at 382 nm in MeOH. 300 MHz $^1$H NMR indicated none of the Schiff base was present.

9) Conversion of Amphotericin B Schiff Base to Free Base

A mixture of amphotericin B methyl ester and its p-chlorobenzilidine derivative (1.1228 g) and Girard's T reagent (0.2619 g) were dissolved in 40 ml THF/H$_2$O (4/1) and stirred for several hours at room temperature. Water (30 ml) was added and THF was removed as an azeotrope at reduced pressure and 40° C. to afford a yellow precipitate which was separated by centrifuge, washed with water, and freeze-dried as an aqueous slurry. Losses were apparent from colloid formation. Yield was 0.449 g of yellow powder, $E^{1\%}_{1\ cm}$=1515 at 382 nm in MeOH.

The above experiment was repeated using 2.025 g of the mixture of free base/Schiff base and 0.5596 g of Girard's reagent in 80 ml THF/H$_2$O (4/1). After addition of water (80 ml) and removal of the THF, the aqueous suspension of the precipitate was dialyzed against water using Spectro/Por® membrane (MWCO:1000) to remove the water-soluble N-p-chlorobenzyilidine derivative of the Girard T reagent. The aqueous suspension of the precipitate retained within the membrane was freeze-dried to obtain 1.2455 g of yellow powder, $E^{1\%}_{1\ cm}$=1500 at 382 nm in MeOH.

10) Amphotericin B Methyl Ester Acetate

A mixture of amphotericin B methyl ester and its p-chlorobenzilidine derivative (1.029 g) was dissolved in 40 ml o THF/H$_2$O (4/1) and 0.90 ml of 1.0 M acetic acid solution was added dropwise. Water (40 ml) was added and THF was removed as an azeotrope at reduced pressure and 40° C. The resulting aqueous solution was passed through a column of Amberlite® XAD-2, then freeze-dried to afford 0.654 g of the acetate salt: $E^{1\%}_{1\ cm}$=1100 at 382 nm in MeOH; a 1% solution had pH 5.30.

11) Amphotericin B Methyl Ester Propionate

The treatment of Example 9 uses one equivalent of propionic acid to give the desired salt.

12) Ampotericin B Methyl Ester Hydrochloride from the Pure Free Base

The relatively pure amphotericin B methyl ester (0.1588 g from Example 9 above) was dissolved in 4.0 ml of THF/H$_2$O (4/1) and the solution stirred as 1.0 ml of 0.1 N hydrochloric acid was added dropwise. Water (4.0 ml) was added and THF was removed as an azeotrope at reduced pressure and 40° C. The resulting aqueous solution was freeze-dried to obtain 0.1483 g of the yellow hydrochloride salt, $E^{1\%}_{1\ cm}$=1361 at 382 nm in MeOH.

In addition to the above examples, it should be recognized that the preparation of the mixture for reacting with the aldehyde, to which cesium carbonate is added, uses, in addition to amphotericin B, nystatin, pimaricin, and their derivatives the following: amphotericin A, rimocidin. Accordingly, using amphotericin B methyl ester as the polyene, the free base-Schiff base mixture is converted, in a single phase liquid reaction, to amphotericin methyl ester hydrochloride, amphotericin methyl ester acetate, amphotericin methyl ester propionate, amphotericin methyl ester ascorbate, and amphotericin methyl ester succinate, or some other salt form, by using tetrahydrofuran in water to dissolve the mixture for acid treatment to obtain the salt.

The acid treatment is performed using an acid selected from the group consisting of aspartic, propionic and acetic acids, or, in addition, selected from the group consisting of hydrochloric acid ascorbic acid, and succinic acid.

The foregoing descriptions and examples are considered to disclose the present invention, but the limits of that invention are to be provided only by the following claims:

What is claimed is:

1. A process for preparing esters of polyene macrolides comprising:

(a) Reacting a mixture containing an amphoteric polyene macrolide antifungal selected from the group consisting of amphotericin B, nystatin, pimaricin, amphotericin A, rimocidin, partricin, and derivatives of said antifungals and anhydrous dimethylformamide with an aldehyde followed by the addition of cesium carbonate and methyl iodide, thereafter precipitating with tertiary-butylmethyl ether, and then stirring in water to produce a free base-Schiff base mixture of the methyl ester;

(b) Converting the free base-Schiff base mixture in a single phase liquid reaction, to a salt form by using tetrahydrofuran and water to dissolve the free base-Schiff base mixture, thereafter neutralizing to obtain the salt form;

(c) Removing the tetrahydrofuran by azeotroping, and recovering the water soluble salt of the polyene methyl ester in the water; and (d) Removing aldehyde liberated during salt formation by centrifuging and eluting the solution through the reverse phase adsorbent to remove residual aldehyde, and then freeze drying to produce the product.

2. The process according to claim 1, wherein the neutralization is performed using an acid selected from the group consisting of propionic acid, acetic acid, hydrochloric acid, ascorbic acid, and succinic acid.

3. The process according to claim 1, wherein the amphoteric polyene macrolide antifungal is amphotericin B.

4. The process according to claim 2, wherein, using amphotericin B methyl ester as the polyene, the polyene ester salts from the acids are selected from the group consisting of amphotericin B methyl ester hydrochloride, amphotericin B methyl ester acetate, amphotericin B methyl ester propionate, amphotericin B methyl ester ascorbate, and amphotericin B methyl ester succinate.

5. A process for preparing esters of polyene macrolides comprising:

(a) Reacting a mixture containing an amphoteric polyene macrolide antifungal selected from the group consisting of amphotericin B, nystatin, pimaricin, amphotericin A, rimocidin, partricin and derivatives of said antifungals and anhydrous dimethylformamide with an aldehyde followed by the addition of cesium carbonate and methyl iodide, thereafter precipitating with tertiary-butylmethyl ether, and then stirring in water to produce a free base-Schiff base mixture of the methyl ester;

(b) Converting the free base-Schiff base mixture of the ester to the relatively pure free base of the ester by use of bisulfite or Girards T reagent and dialysis;

(c) Converting the free base in a single phase liquid reaction to a salt form by using tetrahydrofuran and water to dissolve the free base, thereafter neutralizing to obtain the salt form;

(d) Removing the tetrahydrofuran by azeotroping, and recovering the water soluble salt of the polyene methyl ester in the water by freeze drying.

6. The process according to claim 1, wherein the salt form resulting from said conversion in step (b) is amphotericin B methyl ester hydrochloride.

7. The process according to claim 5, wherein the salt form resulting from said conversion in step (c) is amphotericin B methyl ester hydrochloride.

* * * * *